(12) United States Patent
Domb et al.

(10) Patent No.: US 8,143,368 B2
(45) Date of Patent: Mar. 27, 2012

(54) DISPOSABLE MEDICAL SUPPLIES FROM HYDROLYTICALLY BIODEGRADABLE PLASTICS

(75) Inventors: Abraham J. Domb, Efrat (IL); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/722,655

(22) PCT Filed: Dec. 22, 2005

(86) PCT No.: PCT/US2005/046922
§ 371 (c)(1),
(2), (4) Date: Jun. 6, 2008

(87) PCT Pub. No.: WO2006/071813
PCT Pub. Date: Jul. 6, 2006

(65) Prior Publication Data
US 2008/0255267 A1  Oct. 16, 2008

Related U.S. Application Data

(60) Provisional application No. 60/638,107, filed on Dec. 23, 2004, provisional application No. 60/675,208, filed on Apr. 27, 2005.

(51) Int. Cl.
*C08G 63/54* (2006.01)
(52) U.S. Cl. ............... 528/295.3; 428/35.7; 428/364; 428/365; 428/480; 525/437; 525/440.1; 528/80; 528/81; 528/83; 528/272; 528/288; 528/289; 528/300; 528/301; 528/302; 528/306; 528/307; 528/308; 528/308.6
(58) Field of Classification Search ........... 428/364, 428/35.7, 365, 480; 525/437, 440; 528/80, 528/81, 83, 272, 288, 289, 300, 301, 302, 528/306, 307, 308, 308.6; 606/230
See application file for complete search history.

(56) References Cited

U.S. PATENT DOCUMENTS

| | | | | |
|---|---|---|---|---|
| 2,999,851 | A * | 9/1961 | Elmer | 528/83 |
| 4,032,993 | A * | 7/1977 | Coquard et al. | 623/23.71 |
| 4,100,309 | A * | 7/1978 | Micklus et al. | 427/2.28 |
| 4,594,407 | A * | 6/1986 | Nyilas et al. | 528/272 |
| 4,999,417 | A | 3/1991 | Domb | |
| 5,010,167 | A | 4/1991 | Ron et al. | |
| 5,109,107 | A | 4/1992 | Vora et al. | |
| 5,171,812 | A | 12/1992 | Domb | |
| 5,179,189 | A | 1/1993 | Domb et al. | |
| 5,317,079 | A | 5/1994 | Domb et al. | |
| 5,486,591 | A * | 1/1996 | Domb et al. | 528/272 |
| 6,083,243 | A * | 7/2000 | Pokropinski et al. | 606/230 |
| 6,120,895 | A | 9/2000 | Kowitz et al. | |
| 6,231,970 | B1 | 5/2001 | Andersen et al. | |
| 6,306,403 | B1 | 10/2001 | Donovan | |
| 6,440,106 | B1 | 8/2002 | Yoon | |
| 7,317,069 | B2 * | 1/2008 | Aoshima et al. | 528/275 |
| 2002/0052445 | A1 * | 5/2002 | Terada et al. | 525/185 |
| 2004/0002729 | A1 * | 1/2004 | Zamore | 606/194 |

FOREIGN PATENT DOCUMENTS

| | | |
|---|---|---|
| EP | 0 598 131 | 5/1994 |
| EP | 1136510 | * 3/2001 |
| WO | WO 90/15586 | 12/1990 |
| WO | WO 93/05096 | 3/1993 |
| WO | WO 96/22270 | 7/1996 |
| WO | WO 99/12990 | 3/1999 |
| WO | WO 2004/104067 | * 2/2004 |

OTHER PUBLICATIONS

Duffus, J.H.; Pure Appl. Chem., vol. 74, No. 5, p. 793-807, 2002.*
Teomim, D.; Domb, A.J.; J. Polym. Sci. A: Polym. Chem., vol. 37, p. 3337-3344, 1999.*
Bremer & Osmundsen, "Fatty acid oxidation and its regulation," in *Fatty Acid Metabolism and Its Regulation* (Numa, ed.) Elsevier: New York, p. 113-154 (1984).
Dang, et al., "Effects of Gliadel wafer initial molecular weight on the erosion of wafer and release of BCNU," *J. Control. Rel.* 42: 83-92 (1996). Domb & Langer, "Polyanhydrides. I. Preparation of high molecular weight polyanhydrides," *J. Polym. Chem.* 25: 3373-3386 (1987).
Domb & Maniar, "Absorbable biopolymers derived from dimer fatty acids," *J. Polym, Sci: Polymer Chem.* 31: 1275-1285 (1993).
Domb, et al., "Poly(anhydrides). 3. Poly(anhydrides) based on aliphatic-aromatic diacids," *Macromolecules* 22: 3200 (1989).
Domb, et al., "Polyanhydrides as carriers of drugs" in *Biomedical Polymers: Designed-to-Degrade Systems* (Shalaby,.ed.) Hanser Publishers: Munich, p. 69-96 (1994).
Domb, et al., "Polyanhydrides" in *Handbook of Biodegradable Polymers* (Domb, et al., eds.) Hardwood Academic Publishers, p. 136-159 (1997).

(Continued)

*Primary Examiner* — James J Seidleck
*Assistant Examiner* — Robert Jones, Jr.
(74) *Attorney, Agent, or Firm* — Pabst Patent Group LLP

(57) ABSTRACT

Hydrolytically degradable polymers in the form of biodegradable disposable medical devices for use in medicine and laboratories such as syringes, test tubes, catheters, tubing, trays, medical fabrics, and gloves are described. The devices are formed in whole or in part of a hydrolytically degradable polymer. In the preferred embodiment, the devices or structural components thereof degrade in a period of weeks to months, preferably within a year and more preferably within six months of exposure to aqueous solutions. Conventional hydrolytically degradable polymers may be utilized or these may be modified to increase mechanical or processing characteristics, for example, using a polyfunctional branching agent and/or a chain extending agent. In one embodiment, the hydrolytically degradable polymer is a member of a new class of polyesters comprising an aliphatic dicarboxylic acid, an aliphatic diol and optionally, one or more bifunctional fatty acids such as ricinoleic acid and/or castor oil. The devices are prepared using standard techniques, such as by injection molding, extrusion or melt spinning. The devices can be formed entirely of the degradable polymer, or they can be coated with a polymer coating in order to increase the compatibility of and reduce the possibility for interaction between the surface of the device and liquids that may come in contact with the device, or they may include core or other internal structural member formed of either the biodegradable or non-biodegradable material.

49 Claims, 1 Drawing Sheet

OTHER PUBLICATIONS

Gopferich, in *Handbook of Biodegradable Polymers* (Domb, et al., eds.) Hardwood Academic Publishers, p. 451-471 (1997).

Heller, "Biodegradable polymers in controlled drug delivery," *CRS Crit. Rev, Ther. Drug Carrier Syst.* 1:39-90 (1984).

Hopfenberg, "Controlled release from erodible slabs, cylinders, and spheres" in *Controlled Release Polymeric Formulations* (Paul, et al., eds.) ACS Symposium Series, Washington DC, 33: 26-32 (1976).

Leong, at al., "Polyanhydrides for controlled release of bioactive agents," *Biomaterials* 7: 364-371 (1986).

Mäder, et al., "In vitro/in vivo comparison of drug release and polymer erosion from biodegradable P(FAD-SA) polyanhydrides—a noninvasive approach by the combined use of electron paramagnetic resonance spectroscopy and nuclear magnetic resonance imaging," *Pharm. Res.* 14(6): 820 (1997).

Park, et al., "Biodegradable polyanhydride devices of cefazolin sodium, bupivacaine, and taxol for local drug delivery: preparation, and kinetics and mechanism of in vitro release," *J. Control. Rel.* 52: 179-189 (1998).

Rosen, et al., "Bioerodible polyanhydrides for controlled drug delivery," *Biomaterials* 4: 131-133 (1983).

Teomim, et al., "Fatty acid terminated polyanhydrides," *J. Polym. Sci.* 37: 3337-3344 (1999).

Teomim, et al, "Perivascular delivery of heparin for the reduction of smooth muscle cell proliferation after endothelial injury, " *J. Control Rel.* 60: 129-142 (1999).

Teomim, et al., "Ricinoleic acid-based biopolymers," *J. Biomed. Mater. Res.* 45: 258-287 (1999).

Tirosh, et al., "Oxidative stress effect on the integrity of lipid bilayers is modulated by cholesterol level of bilayers," *Chemistry and Physics of Lipids* 87: 17-22 (1997).

\* cited by examiner

DISPOSABLE MEDICAL SUPPLIES FROM HYDROLYTICALLY BIODEGRADABLE PLASTICS

CROSS-REFERENCE TO RELATED APPLICATIONS

This application is a filing under 35 U.S.C. §371 of PCT/US2005/046922 filed with the U.S. Receiving Office of the Patent Cooperation Treaty on Dec. 22, 2005, which claims priority to U.S. Ser. No. 60/638,107, filed Dec. 23, 2004 and to U.S. Ser. No. 60/675,208, filed Apr. 27, 2005.

FIELD OF THE INVENTION

This invention is in the field of biodegradable disposable medical supplies prepared from hydrolytically degradable polymers.

BACKGROUND OF THE INVENTION

Medical supplies such as syringes, surgical tubing, catheters, test tubes, and collection bags have traditionally been made using thermoplastics such as polyethylene, polystyrene, polypropylene, poly(ethylene terephthalate) and polyvinyl chloride. While these plastics are extremely durable, their disposal can be hazardous to the environment. Thermoplastics such as polyethylene and polypropylene are non-biodegradable and can persist for many years in the environment. Furthermore, such materials are often soiled by biological substances, making recycling of these materials difficult.

As a means of overcoming the problems associated with the disposal of traditional plastic materials, the use of biodegradable plastics has been studied. Biodegradable plastics are degraded into low molecular weight compounds in a relatively short time period by enzymes produced by microorganisms which are found in the environment, including bacteria, fungi and algae. Biodegradable plastics are eventually degraded to small inorganic molecules, such as carbon dioxide and water. Aliphatic polyesters have been used as biodegradable materials in the medical, agricultural and packaging industries. However, such conventional aliphatic polyesters have several potential drawbacks including low crystallinity, low melting points, poor tensile and tear strengths, and difficulties in molding due to their high melt indices. Such disadvantages are due to the relatively low molecular weights that are obtained for these polymers using conventional synthesis techniques. Aliphatic polyesters with number average molecular weights greater than 10,000 have been difficult to produce synthetically using conventional polycondensation chemistry.

There exists a need for biodegradable disposable medical devices that are made from inexpensive starting materials and that can be produced by conventional production processes in order to allow efficient commercialization of such devices.

U.S. Pat. No. 6,440,106 to Yoon describes a biodegradable disposable syringe made from a biodegradable aliphatic polyester composed of an aromatic dicarboxylic acid such as dimethyl terephthalate or terephthalic acid, an aliphatic dicarboxylic acid such as succinic acid and adipic acid, and an aliphatic glycol such as 1,4-butanediol or ethylene glycol. Yoon requires the use of heavy metal catalysts such as antimony acetate, dibutyltin oxide and tetrabutyltitanate in order to prepare polymers with a number average molecular weight greater than 10,000. Residual amounts of these catalysts may leach out of the device during storage or use resulting in contamination of fluids which come in contact with the device.

It is an object of the invention to provide improved biodegradable disposable medical devices that are not implanted into the body.

It is further an object of the invention to provide biodegradable disposable medical devices that do not degrade or leach out toxic materials during storage and use.

It is a further object of the invention to provide methods of making improved biodegradable disposable medical devices.

BRIEF SUMMARY OF THE INVENTION

Hydrolytically degradable polymers in the form of biodegradable disposable medical devices for use in medicine and laboratories such as syringes, test tubes, catheters, tubing, collection bags, trays, packaging materials, medical fabrics, and gloves are described herein. The devices are formed in whole or in part of a hydrolytically degradable polymer. In the preferred embodiment, the devices or structural components thereof degrade in a period of weeks to months, preferably within a year, and more preferably within six months following exposure to aqueous solutions. Conventional hydrolytically degradable polymers may be utilized or these may be modified to improve mechanical or processing characteristics, for example, using a polyfunctional branching agent and/or a chain extension agent. The polyfunctional branching agent increases the number of free reactive functional groups that can react with the chain extension agent. Upon curing, the chain extension agents further polymerize, increasing the mechanical strength and processability of the final polymer without the use of transitional metal catalysts, such as stannous octoate and aluminum isopropoxide. In one embodiment, the hydrolytically degradable polymer is a member of a class of polyester comprising an aliphatic dicarboxylic acid, an aliphatic diol and optionally, one or more bifunctional fatty acids such as ricinoleic acid, and/or castor oil.

The devices can be prepared using standard techniques, such as by injection molding, extrusion or melt spinning. The devices can be formed entirely of the degradable polymer. Optionally, the devices are coated with a polymer coating to increase the compatibility of and reduce the possibility for interaction between the surface of the device and liquids, such as bodily fluids, that may come in contact with the device. In a further embodiment, the devices contain a core or other internal structural member formed of either the biodegradable or a non-biodegradable material.

DETAILED DESCRIPTION OF THE INVENTION

I. Definitions

Figure 1:
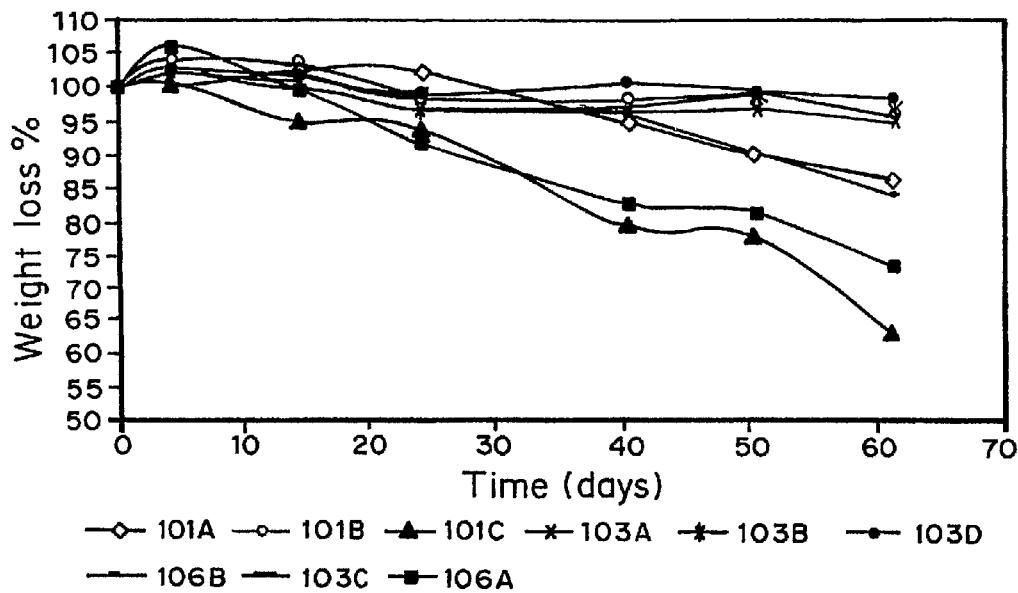
FIG. 1 is a graph of weight % loss during the hydrolytic degradation of 9 different polymers over time (days). Polymer sheets were placed in 0.1M phosphate buffer solution, pH=7.4, at 37° C.

"Biodegradable devices" as used herein refers to devices or the structural components thereof, which degrade in a period of weeks to months, preferably within a year, and more preferably within six months, of exposure to aqueous solutions, such as a 0.1M phosphate buffer solution at about pH 7 at room temperature with shaking at 100 rounds per minute.

"Hydrolytically degradable polymers" as used herein refers to polymers which degrade by hydrolysis. These polymers are preferably biocompatible as defined by the appropriate regulatory agencies such as the U.S. Food and Drug Administration and the U.S. Environmental Protection Agency.

"Branching agents" as used herein refers to molecules that are used to increase the number of free hydroxyl groups in the prepolymer used to form the polymer.

"Chain extension agents" as used herein refers to highly reactive extension molecules having two or more reactive functional groups that react with hydroxyl groups to form new bonds that increase the molecular weight of the prepolymer.

"Elastomeric" as used herein refers to a material that at room temperature can be stretched repeatedly to at least twice its original length, and upon release of the stress, will return with force to its approximate original length.

"Additive" as used herein refers to any compound that is added to the polymer during compounding including fillers, colorants, stabilizers, etc.

"Condensation polymer" as used herein refers to a polymer that is formed upon multiple chemical reactions between monomers that may result in the loss of a small molecule, such as water, during polymerization.

"Curing agent" as used herein refers to a catalytic or reactive agent that brings about polymerization when added to a polymer resin.

"Prepolymer" as used herein refers to a polymer or oligomer capable of undergoing further polymerization via reactive groups on the prepolymer.

"Polymer blend" as used herein refers to a macroscopically homogeneous mixture of two or more different species of polymer.

"Polymer complex" as used herein refers to polymers that interact with each other by electrostatic, Van der Waals, hydrophobic or hydrophilic interactions, stereoselective interactions, or hydrogen bonding.

II. Polymer Compositions

A. Biodegradable Polymers

The biodegradable disposable devices described herein are made, in whole or in part, from hydrolytically degradable polymers. The polymers do not contain leachable toxic catalysts or monomers, such as heavy metal catalysts. The polymers are selected to have physical and mechanical properties that fit the particular application of interest. For example, for test tubes, the polymers should be rigid and tough; while for tubing and collection bags, the polymers should be flexible and transparent. Thus, the molecular weight, the degree of crosslinking, the chemical structure, and other parameters can be adjusted to fit each specific application. The polymers are preferably biocompatible with the degree of compatibility depending on the specific application. For example, polymer compositions that will come in contact with blood or blood components, such as catheter tubing, should be highly biocompatible and inert so that the blood is not affected by the device during use. The polymers may be combined in blends with other biodegradable polymers and/or mixed with additives in order to manipulate the degradation and mechanical properties of the material. In one embodiment, the polymers have a number average molecular weight greater than 20,000 Daltons.

i. Hydrolytically Degradable Polymers

Examples of hydrolytically degradable polymers that are commercially available and are described in the literature, include aliphatic polyesters such as poly(lactic acid), poly (glycolic acid) and poly(lactic acid-co-glycolic acid); poly (trimethylene carbonate); polydioxanone and copolymers; poly(butylenes succinate) (such as polybutylene succinate/adipate copolymers, sold as BIONOLLE®, Showa High-polymer Co. Ltd.) and poly(butylene adipate); polyanhydrides, such as poly(adipic anhydride) and poly(sebacic acid-co-1,3-bis(p-carboxyphenoxy) carboxyphenoxy) propane; poly(ortho ester)s; poly(ester amide)s, such as polymers based on 1,4-butanediol, adipic acid, and 1,6-aminohexanoic acid (BAK1095, Bayer AG, Leverkusen); poly(ester urethane)s; poly(ester anhydride)s; poly(ester carbonate)s, such as tyrosine-poly (alkylene oxide)-derived poly(ether carbonate)s; polyphosphazenes, polyarylates, such as tyrosine-derived polyacrylates; poly(ether ester)s, such as poly(butylene terephthalate)-poly(ethylene glycol) copolymers (PolyActiveo®), poly(ϵ-caprolactone)-poly(ethylene glycol)) block copolymers and poly(ethylene oxide)-poly(hydroxy butyrate) block copolymers; polypropylfumerates; polyacetals; polyethers; biodegradable polycyanoacrylates; biodegradable polyurethanes; polyphosphoesters; poly(amide-enamines); polyamides; poly(amino acids); polycaprolactones; and polyhydroxyalkanoates. For example, specific biodegradable polymers that may be used include, but are not limited to, polylysine, poly (lactic acid) (PLA), poly (glycolic acid) (PGA), copolymers and mixtures of PLA and PGA, e.g., poly (lactide-co-glycolide) (PLG), poly (caprolactone) (PCL), poly (lactide-co-caprolactone) (PLC), and poly (glycolide-co-caprolactone) (PGC).

ii. Fatty Acid-Based Polyesters

In one embodiment, the biodegradable polymer is a fatty-acid containing polyester. These polyesters are prepared by the condensation of an aliphatic diol, an aliphatic or unsaturated dicarboxylic acid, and one or more fatty acids and/or fatty acid containing molecules to form a prepolymer with an initial number average molecular weight of at least 5,000 Da. The addition of fatty acid monomers, such as ricinoleic acid, castor oil, or polyol-partial fatty acid esters having two or more hydroxy, carboxylic acid or amine groups can increase the pliability, flexibility, hydrophobicity, smoothness, and other desired properties of the resulting material. Increased flexibility is ideal for applications such as surgical tubing, catheters, and collection bags. In one preferred embodiment, the biodegradable device is surgical tubing, a catheter, or a collection bag comprising a fatty-acid containing polyester.

Suitable aliphatic dicarboxylic acids include malonic, succinic, glutaric, adipic, sebacic, pimelic, suberic and azelaic acid. Suitable unsaturated diacids include fumaric acid, itaconic acid, and maleic acid. Long chain diacids having more than 10, more than 15, more than 20, and more than 25 carbon atoms such as dimer oleic acid and dimer erucic acid and polycarboxylic acids such as trimer erucic or trimer oleic acids, polyacrylic acid derivatives and citric acid can also be used. The dicarboxylic acids may also contain reactive functional groups, such as amino or hydroxyl groups, which will increase the number of sites available for cross-linking.

Aliphatic diols include 1,2-ethanediol, 1,3-propanediol, 1,4-butanediol, 1,5-pentenediol, 1,5-pentanediol, neopentyl glycol, 1,6-hexanediol, 1,7-heptanediol, 1,8-octanediol, 1,10-decanediol, 2-methyl-1,3-propanediol, 2,2-dimethyl-1,3-propanediol, 3-methyl-1,5-pentanediol, 2-butyl-2-ethyl-1,3-propanediol, 2-butene-1,4-diol, ether diols such as diethylene glycol, triethylene glycol, tetraethylene glycol, dibutylene glycol, tributylene glycol, tetrabutylene glycol, dihexylene glycol, trihexylene glycol, tetrahexylene glycol and oligomer mixtures of alkylene glycols, such as diethylene glycol.

The preferred monomers are inexpensive and available in large quantities so that the polymers used to manufacture the medical devices can be prepared at a cost competitive with current non-degradable devices, such as syringes, test tubes, bags, and other medical supplies.

Fatty acids are suitable for the preparation of biodegradable polymers as they are natural body components. Most fatty acids, however, are monofunctional and cannot serve as monomers for polymerization. Bifunctional fatty acids such as ricinoleic acid can be polymerized to form polyesters without modification. Unsaturated fatty acids such as oleic acid, linoleic acid, and erucic acid can be modified to introduce a hydroxyl group or can be further polymerized through the double bond.

Fatty acids may also include triglycerides that have been partially transesterified with a polyol such as glycerol, mannitol, sorbitol, pentaerythritol, and trihydroxycyclohexane that possess two or more hydroxyl groups per molecule as well as triglycerides that have been partially amidated with polyamines, such as hexantriamine. Triglycerides found in vegetable oils, for example, soybean oil, palm oil, olive oil and sesame oil can also be used.

Ricinoleic acid (cis-12-hydroxyoctadeca-9-enoic acid) is a $C_{18}$ fatty acid with a cis-configured double bond in the $9^{th}$ position and a hydroxyl group in the $12^{th}$ position. Crude ricinoleic acid can be purchased commercially or prepared by the hydrolysis of castor oil. Castor oil is a natural triglyceride that contains on average about 3 hydroxyl groups per molecule. Castor oil is extracted from castor beans, typically by pressing, and is approximately 90% ricinoleate (12-hydroxyoleate).

Oleic acid is a $C_{18}$ monounsaturated fatty acid with a cis-configured double bond in the $9^{th}$ position. Oleic acid is found in animal and vegetable oils and occurs naturally in greater quantities than any other fatty acid. It is present as glycerides in most fats and oils. Erucic acid is a $C_{22}$ monounsaturated fatty acid with a cis-configured double bond in the $13^{th}$ position. Erucic acid is isolated from seed oils such as rape seed, wallflower seed, or mustard seed. Dimer and trimer fatty acids such as dimer oleic or erucic acid are available from UNIQEMA® under the brand name PRIPOL®.

Soybean oil is extracted from soy beans and contains primarily linolenic acid. Linolenic acid is a $C_{18}$ fatty acid with double bonds in the $9^{th}$, $12^{th}$, and $15^{th}$ positions.

Other suitable bifunctional monomers include urea and ethanol amine. These materials are inexpensive and safe. They may be added to increase the mechanical strength of the resulting device.

In one embodiment, the biodegradable polymer is a polyester comprising adipic acid, hexanediol, and ricinoleic acid. Ricinoleic acid is preferably present in an amount from 1% (wt/wt) to about 25% (wt/wt) of the total composition. Adipic acid and hexandiol are preferably present in a range of 75 to 100% (wt/wt) of the polymer composition. In a preferred embodiment, the biodegradable polymer is a polyester comprising adipic acid, hexanediol, and ricinoleic acid in a molar ratio of 1.0:1.0:0.1. In another embodiment, the biodegradable polymer is a polyester comprising adipic acid, butanediol, and 5-10% w/w castor oil.

iii. Modification of Polymer Properties

Any reactive prepolymer having two or more hydroxyl or amino groups can be modified with a branching agent, chain extension agent or curing agent in order to crosslink, branch or extend the prepolymer chains. The molecular weight of the prepolymers, such as fatty acid-based prepolymers, can be increased without the use of the heavy metal catalysts by reacting the prepolymer with a branching agent, such as a polyol, to increase the number of free hydroxyl groups and then further polymerizing the prepolymers in the presence of a chain extension agent such as a diisocyanate. The concentration of the branching agent is from about 1% to about 20% w/w. The concentration of the chain extension agent is from about 1% to about 10% w/w. Upon casting and curing, the polymer chains crosslink resulting in up to a three-fold increase in the molecular weight of the final polymers. The polymer is cast and/or cured at a temperature from about 100° C. to about 200° C. at ambient pressure for a period ranging from several minutes to several hours depending on the polymer.

a. Branching Agents

Hydrolytically degradable polymers can be modified with branching agents. To increase mechanical strength and improve processability, branching agents are used to increase the number of free hydroxy groups in the polymer that are available for crosslinking. The use of branching agents in conjunction with chain extending agents allows for an increase in the mechanical strength of the polymer by increasing the molecular weight of the polymers through crosslinking without the use of heavy metal catalysts.

Examples of branching agents include polyols having number average functionalities of from about 2 to about 100, preferably from 2 to 6. Examples of suitable polyols include: 1,1,1-trimethylolpropane, triethanolamine, glycerol, mannitol, sorbitol, sucrose, sorbitan and pentaerythritol as well as polyvinyl alcohol, polysaccharides, and triglycerides which have been partially transesterified with a polyol.

In a typical synthesis, dicarboxylic acid monomer compositions are added to a polymerization vessel. An equivalent amount of diol monomer is added to the vessel, along with 0.1%-1% w/w of an acid catalyst, and the monomers are polymerized under vacuum at temperatures between about 150 and 200° C. Examples of acid catalysts include sulfuric acid and phosphoric acid. One or more hydroxy fatty acids or fatty acid containing molecules with two or more hydroxyl, amine or carboxylic acid groups are added to the polymer melt in an amount between about 1% and about 20% by weight and the melt polymerization process is continued until full incorporation of these components into the polymer is achieved. A polyol, such as glycerol, glycerol monoglyceride, or poly(vinyl alcohol), is added to the vessel and the melt is heated for a short time, typically from a few minutes to about one hour depending on the reaction temperature, to avoid crosslinking.

b. Chain Extension Agents

The prepolymers can be further polymerized in the presence of a chain extension agent. Chain extension agents typically have two or more reactive functional groups that efficiently react with hydroxyl groups to form new bonds that increase the molecular weight of the prepolymer. Such molecules include organic molecules having two or more isocyanate groups (e.g. diisocyanates), epoxide groups (e.g. diepoxides), and reactive derivatives of carboxylic acids such as anhydrides (e.g. dianhydrides), diethyl carbonate, chlorides and reactive esters. Other reactive groups the can be attached to the prepolymer include vinyl groups such as acrylic or methacrylic acid anhydrides or reactive methyl or ethyl esters. Preferably the extension agents do not release a small molecule upon reaction.

In a typical synthesis, the prepolymer is mixed with a chain extension agent and melt polymerized at a temperature between about 100° C. to about 200° C. The concentration of the chain extension agent is from about 1% to about 10% by weight. The modified polymer contains reactive functional groups which react upon injection molding to increase the mechanical strength of the resulting molded articles. In one embodiment, a prepolymer containing adipic acid, butanediol, and 5-10% w/w ricinoleic acid or castor oil is mixed with 5-10% w/w hexamethylene diisocyanate (HMDI or HMD) and melt polymerized at 155° C. for 15 minutes.

The resulting prepolymer containing a chain extension agent, may contain some reactive groups, such as an isocyanate, epoxide, carbonate or anhydride group, which can be further polymerized during or after molding of the device for curing and setting the final shape and properties of the device. For example, the reactive polymer is isolated from the polymerization vessel and chopped into flakes and packed for the fabrication molding step. Upon casting and curing, the polymer chains can crosslink or branch due to the presence of the chain extension agent thus increasing the molecular weight of the polymer. The polymers may be combined with other polymers, in blends and complexes prior to casting, in order to manipulate the degradation and mechanical properties of the material.

Isocyanates

Suitable isocyanates include aliphatic, cycloaliphatic and aromatic polyfunctional isocyanates, particularly difunctional isocyanates having from 2 to 18 carbon atoms, preferably between 4 and 14 carbon atoms, such as 1,6-hexamethylene diisocyanate, 1,4-tertramethylene diisocyanate, ethylene diisocyanate and 1,12-dodecane diisocyanate, 5-isocyanato-1-(isocyanatomethyl)-1,3,3-trimethylcyclohexane (isophorone diisocyanate (IPD), mixture of isomers), 1,3-bis (1-isocyanato-1-methylethyl)benzene, cyclohexane-1,3-diisocyanate, cyclohexane-1,4-diisocyanate as well as mixtures thereof, 4,4'- and 2,4-diisocyanatodicyclohexylmethane and 1,3- and 1,4-phenylene diisocyanate and mixtures thereof. The preferred isocyanates are 5-isocyanato-1-(isocyanatomethyl)-1,3,3-trimethylcyclohexane (isophorone diisocyanate, mixtures of isomers), 1,3-bis(1-isocyanato-1-methylethyl) benzene, aliphatic isocyanate such as hexamethylene diisocyanate (HMDI or HMD) and mixtures thereof. The preferred polymers are essentially aliphatic but may contain a small amount, preferably up to 5% by weight, of aromatic residues, such as toluene diisocyanate and phthalic acids.

In one embodiment, 5-10% w/w HMDI is reacted with a prepolymer of adipic acid, butanediol, and 5-10% w/w ricinoleic acid or castor oil. In a typical synthesis, diacid monomer compositions are added to a polymerization vessel. An equivalent amount of diol monomers is added to the vessel, along with 0.1%-1% w/w of an acid catalyst, and the monomers are polymerized under vacuum at temperatures between about 150 and 200° C. Examples of acid catalysts include sulfuric acid and phosphoric acid. One or more fatty acids are added to the polymer melt in an amount between about 2% and about 20% by weight and the melt polymerization process is continued until full incorporation of these components in the polymer is achieved. A polyol such as glycerol, glycerol monoglyceride, or poly(vinyl alcohol) is added to the vessel and the melt is heated for a short time, typically a few minutes to about one hours depending on the reaction temperature, to avoid crosslinking. The polymer is isolated from the polymerization vessel and chopped into flakes and packed for the fabrication molding step. The prepolymers may be combined with other polymers, as discussed above, in blends and adducts to manipulate the degradation and mechanical properties of the material. In one embodiment, the prepolymer comprises adipic acid, butanediol and 5-10% ricinoleic acid or castor oil.

The reaction of diisocyanates with the free hydroxyl groups on the polymer is spontaneous and rapid without the release of by-products. The reaction can be performed at ambient pressure without the need for catalysts. The reaction kinetics are directly influenced by the reaction temperature, which allows for control of the reaction time to obtain polymers with the desired molecular weight.

iv. Additives

For the production of highly durable syringes and other medical supplies, the biodegradable polymers may be combined with strength increasing additives such as talc, calcium carbonate, magnesium stearate, calcium sulfate, starches, sugar powder, particulate anhydrous silicates, clay, sand, silicates, cellulose powder, carbon powder, silicon dioxide, calcium phosphate, and synthetic and natural resins. The additives are typically present in an amount ranging from about 1% to about 70% by weight of the polymers(s). In a preferred embodiment, the additive is talc or calcium carbonate. While calcium carbonate is inferior to talc in fortifying strength, it can be used as a fertilizer and prevent acidification of the soil upon degradation of the polymer. In addition, the combustion rate of the polymers containing calcium carbonate is better than the combustion rate of the polymer alone or polymers containing talc.

v. Polymer Blends and Complexes

The polymers may be combined with other polymers in blends and adducts to manipulate the degradation and mechanical properties of the material. Practically any biocompatible polymer may be used. In a preferred embodiment, the added polymer is biodegradable. Exemplary biodegradable polymers include natural polymers and their synthetic analogs, including polysaccharides, proteoglycans, glycosaminoglycans, collagen-GAG, collagen, fibrin, and gelatin. Hydrolytically degradable polymers are listed above.

III. Manufacture of the Biodegradable Polymers

The resulting polymers can be injection molded, extruded, melt spun or cast, or solvent cast into the desired shapes. These methods are known to those skilled in the art. For example, the hydrolytically degradable polymer(s) can be dry mixed with one or more curing agents, and optionally with a filler such as oxidized starch or cellulose, and fed into an injection molding system where the polymer is molded at high temperature to allow crosslinking. Examples of curing agents include polyanhydrides such as poly(adipic anhydride) and poly(sebacic anhydride). The fabricated device can be further cured by annealing in a hot oven.

The biodegradable polymers described herein are used are used to form safe, biocompaticle, biodegradable devices. The resulting devices do not provoke an adverse reaction when contacted with bodily fluids, such as blood, solid or liquid medications. Additionally, the devices may be designed so that they do not absorb the solid or liquid medications or bodily fluids that they contact. This allows for the concentration of a medication stored a biodegradable disposable device to remain constant throughout storage and use. The device can be designed to retain its strength, flexibility, and other mechanical characteristics, throughout use. Thus, the device can be designed so that it does not degrade during use, but degrades when it is disposed. Due to the polymers used to form the devices, the devices do not release toxic molecules, such as toxic heavy metals during use or degradation. Representative biodegradable disposable medical devices that may be formed from the polymers include, but are not limited to, test tubes, infusion sets, catheters, tubing, syringes, collection bags (e.g. blood bags), packaging materials and medical fabrics such as gowns, wound dressings, sutures, clothing, and surgical drapes.

The articles of manufacture can be coated with a polymer coating or laminated before, during, or after fabrication, in order to increase the compatibility of and reduce the possibility for interaction between the surface of the article and the loaded liquids. The use of such a coating reduces the need for high purity of the polymer surface of the device, resulting in lower manufacturing costs.

The article can be coated by rapidly submerging the article to be coated in a solution or melt of the polymer coating and drying the article using warm air. The polymer coating solution can be prepared by dissolving the polymer in a volatile organic solvent, such as methyl ethyl ketone. The concentration of the polymer coating solution is from about 0.1% to about 1.0% w/v. The thickness of the resulting coating is generally between about 1 microns and 200 microns. The polymer coating can also be applied by melt extrusion and spin casting. Suitable coatings materials include non-degradable polymers, such as polyethylene, polypropylene, polyurethanes, poly(vinyl acetate), polymethyl methacrylate, poly(vinyl chloride), poly(vinyl fluoride), polystyrene, polyisobutylene, poly(butadian), poly(acrylonitrile), polysilicones and their copolymers and blends as well as other polymers known for their biocompatibility suitable for the specific device. In a preferred embodiment, the non-degradable coating on the device has a thickness of 100 microns or less. Such a coating may be on the inside of a test tube. It is important that the coating adhere to the base polymeric device. Alternatively, any of the biodegradable polymers listed above are suitable as coatings. In a preferred embodiment, the coating is formed from a slow degrading hydroxyalkanoic acid based polymers with a well established biocompatibility which include: poly(hydroxybutyrate), poly(caprolactone), lactaide based homo and copolymers.

The biodegradable polymer can also be used to form the core of, or structural supports located within, a non-degradable device. Conversely, these core elements or structural features may be formed of non-biodegradable materials within a matrix of biodegradable polymer.

The present invention will be further understood by reference to the following non-limiting examples.

EXAMPLES

Materials

The following materials were used in the Examples: Adipic Acid (99% pure; Fluka, Buch, Switzerland), SA (99% pure; Aldrich, Milwaukee, Wis.), BD (99% pure; Aldrich, Milwaukee, Wis.) and RA (85% pure; Fluka, Buch, Switzerland); Butanediol (99% pure; Sigma-Aldrich, Rehovot, Israel); Ethylene glycol (99% pure; Sigma-Aldrich, Rehovot, Israel); Propylene glycol (99% pure; Sigma-Aldrich, Rehovot, Israel); Rincinoleic acid (85% pure; Fluka, Buch, Switzerland); and Castor Oil (Eur. Ph; Haifa, Israel). All solvents were analytical-grade from Biolab (Jerusalem, Israel) and were used without further purification.

Instrumentation

IR spectroscopy (2000 FTIR, PerkinElmer) was performed on the prepolymer and polymer samples cast on to NaCl plates from a chloroform solution. Thermal analysis was determined on a Stuart Scientific SMP1 meting point heater.

The molecular weights of the polyesters and polyesters-urethanes were estimated on a gel permeation chromatography (GPC) consisting of the a Waters 1515 isocratic HPLC pump with a Waters 2410 refractive-index detector and a Rheodyne (Coatati, Calif.) injective valve with a 20 μL Loop (Waters Ma). The polyester samples were eluted with $CHCl_3$ through a linear Ultrastyragel column (Water; 500-Å pore size) at a flow rate of 1 ml/min. The polyester-urethane samples were eluted with $CHCl_3$ through a linear Ultrastyragel column (Water; 500-Å pore size) at a flow rate of 1 ml/min. The molecular weights were determined relative to polystyrene standards (Polysience, Warrington, Pa.) with a molecular weight range of 9,100-355,000 Da with a breeze computer program.

1H NMR spectra ($CDCl_3$) were obtained on a Varian 300 MHz spectrometer in tubes with 5 mm outside diameters. $CDCl_3$ containing tetramethylsilane served as a solvent and shift reference.

The viscosity of the polymers was determined using the rotational method using a Brookfield Programmable Rheometer (LV-DV-III) with an LV4 cylindrical spindle.

Example 1

Manufacture of a Syringe Composed of Poly(Butylene Glycerol Adipate)

Poly(butylenes-glycerol adipate) was synthesized by polycondensation of butylene glycol, adipic acid, and glycerol (all available from Aldrich) at a 1.5:2:0.5 mole ratio for 5 hours at 150° C. under a vacuum of 50 mTorr. The polymerization yielded a transparent, almost colorless uncrosslinked elastomer that did not swell or dissolve in water. When a butylene glycol:adipic acid:glycerol ratio of 1:1:2 was used, a rigid, crosslinked polymer was obtained. The uncrosslinked polymer was injection molded at 200° C. to form the barrel of a 10 ml syringe.

Example 2

Synthesis of Adipic Acid Based Polyesters

To a 500 ml flask, 60 g of adipic acid and 192 g of succinic acid were added while slowly increasing the temperature to 200° C. and water was effused out. When the temperature reached 200° C., 130 g of 1,4-butanediol and 0.5 g of phosphoric acid, a catalyst, were added to the reaction mixture and the mixture was reacted at 200° C. for 5 hours at 1 mmHg. The biodegradable resin had a number average molecular weight of 22,000, a weight average molecular weight of 60,000 and a melting point of 95° C. as measured by DSC. Other branched polyesters can be prepared in a similar fashion.

Example 3

Synthesis of Prepolymers Based on Adipic Acid and Diols with Ricinoleic Acid or Castor Oil The time, ratio of reagents and use of sulfuric/phosphoric acids as catalysts were investigated in order to prepare prepolymers with the highest Mn/Mw possible. The polymerizations were carried out at temperatures between 180 and 200° C. Table 1 lists the different Number average (Mn) and Weight average (Mw) molecular weights obtained for a variety of adipic acid-based polyesters formed using different reagents and catalysts.

TABLE 1

Number Average and Weight Average Molecular Weights (Da) for Adipic Acid-Based Polyesters

| Mn | Mw | Additional monomers | Monomer II | Monomer I |
|---|---|---|---|---|
| Linear/Branched prepolymers: without any catalyst: 2.5 h at a pressure of 1 mm Hg and a temperature of 180-200° C. | | | | |
| 6712 | 4403 | | Ethylene glycol | Adipic acid |
| 6712 | 4403 | 20% Ricinoleic acid | Ethylene glycol | Adipic Acid |
| 6221 | 2973 | 20% castor oil | Ethylene glycol | Adipic acid |
| 6102 | 3655 | | Propylene glycol | Adipic acid |
| 1353 | 1034 | 20% Ricinoleic acid | Propylene glycol | Adipic acid |
| 2735 | 1555 | 20% castor oil | Propylene glycol | Adipic acid |
| 6712 | 5073 | | Butandiol | Adipic Acid |
| 6712 | 5517 | 20% Ricinoleic acid | Butandiol | Adipic acid |
| 6221 | 4464 | 20% castor oil | Butandiol | Adipic acid |
| Linear prepolymers: 0.1% w/w $H_2SO_4$ as catalyst: 2.5 h $N_2$ + 24 h vacuum | | | | |
| 8396 | 6238 | 20% Ricinoleic acid | Ethylene glycol | Adipic Acid |
| 7530 | 5228 | 20% Ricinoleic acid | Propylene glycol | Adipic acid |
| 8206 | 6167 | 20% Ricinoleic acid | Butandiol | Adipic acid |
| Linear prepolymers: 0.5% w/w $H_2SO_4$ as catalyst: 2.5 h $N_2$ + 24 h vacuum | | | | |
| 8231 | 6029 | 20% Ricinoleic acid | Ethylene glycol | Adipic Acid |
| 5899 | 3499 | 20% Ricinoleic acid | Propylene glycol | Adipic acid |
| 6667 | 4294 | 20% Ricinoleic acid | Butandiol | Adipic acid |
| Linear prepolymers: 1% w/w $H_2SO_4$ as catalyst: 2.5 h $N_2$ + 24 h vacuum | | | | |
| 7210 | 4936 | 20% Ricinoleic acid | Ethylene glycol | Adipic Acid |
| 6640 | 4294 | 20% Ricinoleic acid | Propylene glycol | Adipic acid |
| 6228 | 3539 | 20% Ricinoleic acid | Butandiol | Adipic acid |
| Linear prepolymers: 0.1% w/w $H_3PO_4$ as catalyst: 2.5 h $N_2$ + 24 h vacuum | | | | |
| 5661 | 3434 | 20% Ricinoleic acid | Ethylene glycol | Adipic Acid |
| 2960 | 1757 | 20% Ricinoleic acid | Propylene glycol | Adipic acid |
| 9060 | 7423 | 20% Ricinoleic acid | Butandiol | Adipic acid |
| Linear prepolymers: 0.5% w/w $H_3PO_4$ as catalyst: 2.5 h $N_2$ + 24 h vacuum | | | | |
| 6656 | 4439 | 20% Ricinoleic acid | Ethylene glycol | Adipic Acid |
| 3498 | 2002 | 20% Ricinoleic acid | Propylene glycol | Adipic acid |
| 9490 | 12737 | | Butandiol | Adipic acid |
| 10337 | 13520 | 5% Ricinoleic acid | Butandiol | Adipic acid |
| 10812 | 13589 | 10% Ricinoleic acid | Butandiol | Adipic acid |
| 13521 | 17220 | 15% Ricinoleic acid | Butandiol | Adipic acid |
| 10445 | 9248 | 20% Ricinoleic acid | Butandiol | Adipic acid |
| 10964 | 13788 | 5% Castor Oil | Butandiol | Adipic acid |
| 10643 | 13519 | | Butandiol | Sebacic acid |
| 9621 | 14003 | 5% Ricinoleic acid | Butandiol | Sebacic acid |
| Linear prepolymers: 1% w/w $H_3PO_4$ as catalyst: 2.5 h $N_2$ + 24 h vacuum | | | | |
| 6912 | 5104 | 20% Ricinoleic acid | Ethylene glycol | Adipic Acid |
| 4520 | 2645 | 20% Ricinoleic acid | Propylene glycol | Adipic acid |
| 9773 | 8353 | 20% Ricinoleic acid | Butandiol | Adipic acid |

Ricinoleic acid and sebacic acid were added as w/w.

Characterization of the Polymers

IR

All polymers had typical bands at 1710 (carbonyl groups), 1050-1300 (ester stretching bands) and a band at 3500 suggesting that the prepolymers have hydroxyl terminated chains, which is expected because of the excess of diol used in the polymerization.

NMR

The polyesters based on adipic acid and butanediol showed typical peaks at 1.649 $8H(CH_2)_4$ of the diol and the acid, 2.290 $4H(CH_2)_2$ acid, 4.05 $4H(CH_2)_2$ diol and 3.7 terminal OH groups. Incorporation of ricinoleic acid showed typical peaks at 5.35 (ricinoleic acid double bond) and 4.8 (ricinoleic acid ester), which shows incorporation of ricinoleic acid in the polymer chain.

The polyesters based on sebacic acid and butanediol showed typical peaks at 1.228 $8H(CH_2)_4$ aliphatic chain of the acid, 1.649 $8H(CH_2)_4$ of the diol and the acid, 2.217 $4H(CH_2)_2$ acid, 4.05 $4H(CH_2)$ diol and 3.7 terminal OH groups. Incorporation of ricinoleic acid showed typical picks at 5.35 ricinoleic acid double bond and 4.8 ricinoleic acid ester which shows incorporation of ricinoleic acid in the polymer chain.

Viscosity

Viscosity of the polyesters is property which can affect their processing and production potentials. One of the most obvious factors that can have an effect on the rheological behavior of a material is temperature. Some materials are quite sensitive to temperature, and a relatively small variation will result in a significant change in viscosity. Measuring viscosity at different shear rates is also important when a material is to be subjected to a variety of shear rates in processing or use. The viscosities of four polyesters adipic acid-butane diol (AABD), adipic acid-butane diol-5% ricinoleic acid (AABDRA5%), sebacic acid-butane diol (SABD) and sebacic acid-butanediol-5% ricinoleic acid (SABDRA5%) were measured at temperatures ranging of 130-150° C., in which the polymers were still liquid.

The viscosities of AABD and AABDRA5% were measured at share rates between 8.28 and 1.035 $sec^{-1}$ and different temperatures (ranging from 50° C. to 150° C.). The viscosities of SABD and SABDRA5% were measured at shear rates between 4.04 and 1.035 $sec^{-1}$ and different temperatures (ranging from about 60° C. to about 120° C. for SABD and from about 60° C. to about 140° C.).

All of these polymers showed typical behavior as Newtonian fluids and their viscosities were not affected by the shear rate applied. Further, the incorporation of ricinoleic acid into adipic acid-butanediol polyester reduced the viscosity of the polymers and appeared to contribute to the liquidity of the polymer. However the incorporation of ricinoleic acid into sebacic acid-Butanediol polyester polymer has an opposite effect, and increased the viscosity of the polymers.

Example 4

Enrichment of Adipic Acid-Based Prepolymers with Hydroxyl Groups

The prepolymers of Example 1 were further reacted with glycerol to increase the number of free hydroxy groups. The prepolymers were reacted with glycerol under vacuum at 200° C. Other suitable polyols include mannitol, pentaerithritol, and sorbitol. The number average and weight average molecular weights of the polymers before and after addition of glycerol are provided in Table 2.

TABLE 2

Number Average and Weight Average Molecular Weights of Adipic Acid-Based Polyesters Before and After Addition of Glycerol

| Mn (after addition of glycerol) | Mw | Mn (before addition of glycerol) | Mw | glycerol (% w/w) | Prepolymer |
|---|---|---|---|---|---|
| 8206 | 5637 | 7544 | 5517 | 5 | A.A.[a] + B.D.[b] + R.A.[c] |
| 7440 | 5048 | 4415 | 6563 | 5 | A.A.[a] + B.D.[b] + R.A.[c] |
| 6615 | 3475 | 6774 | 4464 | 8 | A.A.[a] + B.D.[b] + C. oil[d] |

[a] A.A. refers to adipic acid
[b] B.D. refers to butanediol
[c] R.A. refers to ricinoleic acid
[d] C. oil refers to castor oil

Example 5

Increasing the Molecular Weight of the Prepolymers Through Branching and Crosslinking The prepolymers of Examples 1 and 2 were further polymerized to obtain higher molecular weight materials by reacting the prepolymers with highly reactive chain extension molecules having two or more reactive functional groups that efficiently react with hydroxyl groups to form new bonds and thus increase the molecular weight of the prepolymer.

10 grams of butylene adipate-ricinoleate was melted in a round bottomed flask and 1, 5, or 10% w/w hexamethylene diisocyanate was added and mixed well to obtain a uniform melt. The reaction was continued at 140° C. for 5 hours with mixing. After cooling to room temperature, the pliable off-white polymer mass was analyzed for solubility in dichloromethane and the molecular weight of the polymer was determined. The 10% urethane-containing polymer was partially insoluble as it formed a crosslinked gel. The 1 and 5% urethane-containing polymers had molecular weights exceeding 50,000 Da. Similar results were obtained when pyromelittic anhydride and polysebacic anhydride were used at reaction times of about 10 hours. However, the reaction time can be shortened by increasing the reaction temperature or by addition of a catalyst.

The solubilities and the degree of crosslinking for a variety of butylene-adipate polymers reacted with hexamethylene diisocyanate and isophoronediisocyanate are described in Table 3.

TABLE 3

Degree of Cross-linking In Adipic and Sebacic Acid-Based Polyesters

| Prepolymer | Solubility in CHCl₃ | Degree of crosslinking | Characteristics of the soluble part Mn | Mw |
|---|---|---|---|---|
| HMD | | | | |
| AA-BD-RA5% | 5% | Crosslinked | 50.8 | 18842 | 37064 |
| AA-BD-RA10% | 5% | Crosslinked | 85.8 | 23360 | 55084 |
| AA-BD-RA15% | 5% | Crosslinked | 52.1 | 19141 | 38354 |
| AA-BD-CO5% | 5% | Crosslinked | 83.2 | 17793 | 39692 |
| SA-BD | 5% | Crosslinked | 25.2 | 29739 | 73891 |
| SA-BD-RA5% | 5% | Crosslinked | 6.4 | 15388 | 21987 |
| AA-BD-RA5% | 10% | Crosslinked | 98.6 | 14427 | 25077 |
| AA-BD-RA10% | 10% | Crosslinked | 91.9 | 19614 | 38258 |
| AA-BD-RA15% | 10% | Crosslinked | 81.96 | 18852 | 36249 |
| AA-BD-CO5% | 10% | Crosslinked | 96.6 | 16447 | 35262 |
| SA-BD | 10% | Crosslinked | 25.2 | 19859 | 27064 |
| SA-BD-RA5% | 10% | Crosslinked | 97 | 15417 | 29274 |
| IPD | | | | |
| AA-BD | 5% | Crosslinked | 92.6 | 15085 | 22443 |
| AA-BD-RA5% | 5% | Soluble | 0 | 24826 | 47779 |
| SA-BD | 5% | Soluble | 0 | 18575 | 33240 |
| SA-BD-RA5% | 5% | Soluble | 0 | 16258 | 27162 |

Example 6

Degradation Studies of Adipic Acid-Based Polyesters

Polymer samples with the desired mechanical properties were prepared as sheets. To prepare the sheets, poly(butylene adipate) (AABD), poly(butylenes adipate ricinoleate) (AABDRA5%), poly(butylenes succinate) (SABD), poly(butylenes succinate ricinoleate) (SABDRA5%), were cured with either 5% or 10% hexamethylene diisocyanate (HMD) or isophoronediisocyanate (IPD). The polymer compositions were prepared melt mixing the polyesters with HMD or IPD for 20 minutes at 100° C., and the resulting polymers were isolated and placed onto preheated Teflon plates. The polymers were pressed between two plates at temperature above 100° C., and kept under pressure for an additional 10 minutes. After 10 minutes, the polymers were cooled to room temperature.

Hydrolytic Degradation of Polymers

Samples with similar weight were incubated in 40 ml of a 0.1M phosphate buffer (pH=7.4) at 37° C. The buffer was replaced daily to prevent potential saturation. At different time points (5, 15, 25, 40, 50 and 62 days), the buffer was removed, the samples were dried under vacuum for 6 hours and the weight loss of the samples was calculated. The weight loss (%) for the polymers over time (days) is provided in FIG. 1.

Figure 2:
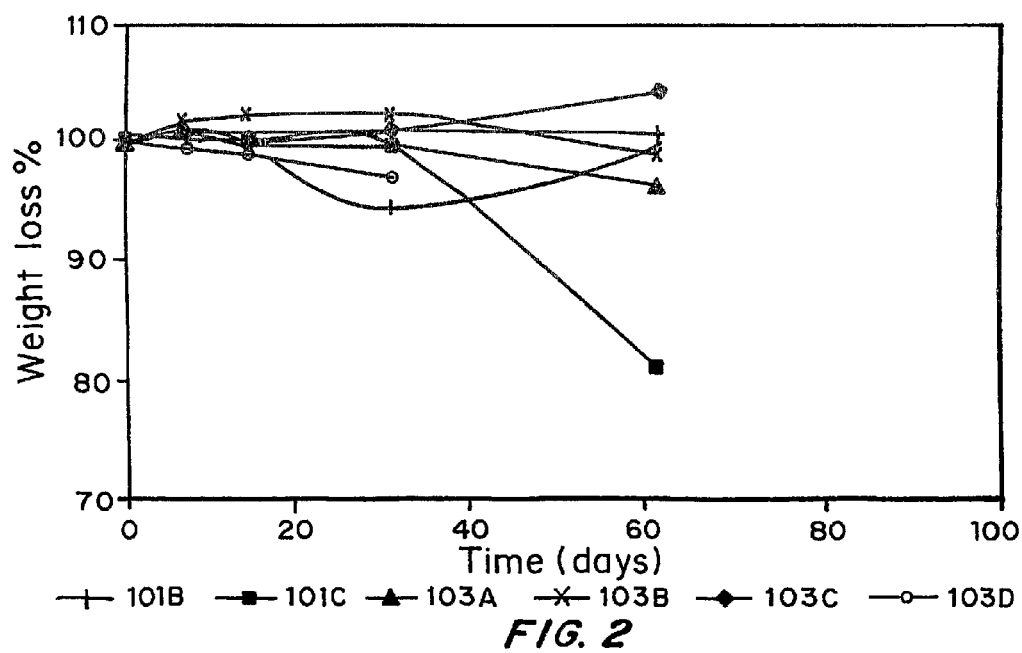
FIG. 2 is a graph of weight % loss for 6 of the polymers tested in FIG. 1 over time (days). Polymer sheets were buried in soil with a temperature was in the range of 25-30° C. during the day and 17-23° C. during the night.

In FIGS. 1 and 2, 101a corresponds with AABD+5% HMD, 101b corresponds with AABDRA5%+5% HMD, 101c corresponding with SABD+5% HMD, 103a corresponds with AABD+10% HMD, 103b corresponds with AABDRA5%+10% HMD, 103c corresponds with SABD+10% HMD, 103d corresponds with SABDRA5%+10% HMD, 106a corresponds with AABD+5% IPD, and 106b corresponds with AABD5RA%+5% IPD.

Biodegradation of the Polymers

In order to evaluate the degradation of the polymers under environmental conditions (i.e. both under the influence of water and enzymatic activity), the degradation studies were conducted in soil outside. The samples were wetted daily to prevent the soil from drying out and inhibiting enzyme activity.

Polymer samples with similar weight were buried in soil at a local garden that was irrigated twice a week. The temperature was in the range of 25-30° C. during the day and 17-23° C. during the night. The samples were wetted daily to prevent the soil from drying out. At 5, 15, 25, 40, 50 and 62 days, the samples were removed, washed and dried overnight and the weight loss of the samples was calculated. The stability of the polymers under environmental conditions is shown in FIG. 2.

Results and Discussion

The incorporation of hydrophobic monomers, such as ricinoleic acid, even at small concentrations affects the rate of hydrolytic degradation for the polymer. The rate of degradation of the polymers with Ricinoleic acid are slower than the same polymers without ricinoleic acid (see e.g. AABD+5% HMD (101a) compared with AABDRA5%+5% HMD (101b) and AABD+5% IPD (106a) compared with AABD5RA%+ 5% IPD (106b)). The effect is more noticeable in the case of AABD+5% IPD compared with AABD5RA%+5% IPD because it would have been expected that the crosslinked polymer, AABD+5% IPD (106a), would degrade more slowly than the linear polymer, AABD5RA%+5% IPD (106b), but the results of this study showed that the hydrophobic nature of the polymers had a greater effect since the polymer without ricinoleic acid degraded faster than the one with ricinoleic acid.

The diisocyanate concentration also affects the degredation rate. The polymers prepared with high concentration of HMD, i.e. AABD+10% HMD (103a), AABDRA5%+10% HMD (103b), and SABD+10% HMD (103c), and SABDRA5%+10% HMD (103(d)), were not sensitive to hydrolytic degradation. The higher amount of HMD eliminated the ability of the polymer to degrade under hydrolytic conditions. For example, when only 5% HMD was present in the polymer, SABD+5% HMD (101c), the polymer degraded throughout the test period, while when 10% HMD was present in the same polymer, SABD+10% HMD (103c), the polymer degraded much more slowly, with degradation being noticeable around 40 days. It appears that the higher amount of HMD increases the density of crosslinking and thereby reduces the ability of water to reach the ester bonds in the polymer. Thus, the amount of diisocyanate used in the polymer can have a significant influence on the polymers degradation rate. The incorporation of the hydrophobic monomers also decreases the degradation potential when the same amount of diisocyanate is used.

Example 7

Manufacture of a Biodegradable Syringe

A mixture of butylene adipate-ricinoleate pre-polymer (Mw=8,400) with 10% hexamethylene diisocyanate, is heated at 150° C. for one hour. After one hour, the melt is injection molded to form a syringe plunger and barrel. The resulting syringe plunger and barrel are cured at 100° C. for 3 hours to yield solid uniform syringe elements that are a translucent off-white. The syringe parts are insoluble in organic solvents, which indicated crosslinking of the polymer chains.

Alternatively, the prepolymer was melt mixed with 30% w/w of starch powder, titanium dioxide, and fine dry oil or fine carbon powder. 10% w/w hexamethylene diisocyanate was added to the melt mix and mixed well. The resulting mixture was injection molded into a syringe mold at 180° C. The resulting syringe parts were cured in a 150° C. oven for 30 minutes to yield uniform and tough plastic syringes.

In another injection molding run, rigid test tubes of 10 mL capacity were produced. The rigid but strong and non-breakable tubes were stable for more than one week when loaded with plasma or saline solutions.

Example 8

Manufacture of Biodegradable Flexible Tubes

A prepolymer was prepared from the condensation of adipic acid, hexanediol, castor oil and ricinoleic acid in a 2:1.4: 0.5:0.5 molar ratio. The condensation reaction was carried out at 200° C. in the presence of 0.1% w/w of phosphoric acid. A semisolid polymer was obtained having a molecular weight of Mw=6,700 and Mn=4,300. The prepolymer was mixed at room temperature with hexamethylene diisocyanate (8% w/w) along with 0.01% $SnCl_2$ and the mixture was melt condensed at 100° C. for 6 hours. The molten polymer having a molecular weight exceeding 50,000 was extruded into flexible tubes having an outer diameter of 3 mm and an inner diameter of 2 mm. Translucent flexible tubes were obtained which allowed for the transport of liquids, such as saline solution.

Example 9

Coating of Rigid Test Tubes

To increase the compatibility and reduce the possibility for interaction between tube walls and liquids in these tubes, the inner surface of the tubes was coated with high molecular weight biodegradable polycaprolactone (Mw>100,000) by rapid passing through the tube interior a solution of polycaprolactone in methylethyl ketone at concentrations of 0.1, 0.5 or 1% w/v. The lumen in the test tube was dried by passing warm air though the lumen to yield a uniform thin coating as determined by Scanning Electron Microscopy (SEM). The thickness of the coating was between 10 microns and 60 microns depending on the polycaprolactone concentration applied.

The coating adhered well to the tube surface and did not affect the flexibility of the tube. The stability of the tube to saline, blood, plasma and urine was determined by filling the tube with one of these liquids and storing the filled tubes at 37° C. for 24 hours. The tubes were emptied and the inner tube surface was examined by SEM. No change in the surface coating was observed. The tubes were placed in an incubator at 40° C. and 100% humidity for 4 weeks to measure the shelf life stability of the tubes. No change in the physical and mechanical properties of the tubes was observed. To determine the hydrolytic degradation of the tubes, samples of coated and uncoated tubes were placed in a buffer solution of pH 7.4 at 37° C. for 20 days. No degradation of the tube was observed. However, when placing the tubes in moisturized agricultural soil at 37° C. for one month, some degradation on the surface of the tubes was observed. Similarly, other biodegradable or non-degradable polymers described above could be applied as a coating for disposable medical devices. Non-degradable biocompatible polymers including polyurethanes, poly(vinyl acetate), polymethyl methacrylate, poly (vinyl chloride), polypropylene, and polyethylene, were applied as inner coatings with a thickness of 100 microns or less.

Example 10

Transesterification of Triglycerides with Mannitol

In order to obtain low cost di-, tri- and tetrahydroxyl monomers, soybean oil was mixed with mannitol at 2:1, 1:1, and 1:2 molar ratios and heated to 100° C. with constant stirring. $H_3PO_4$ (0.1% w/w) was added to the mixture of mannitol and soybean oil and the reaction was continued until a uniform clear mixture was obtained (usually after about 3-5 hours). The product show high hydroxyl content with the degree of hydroxyl groups correlating with the ratio of mannitol used. A similar reaction was carried out for other common plant and vegetable oils as well as hydrogenated vegetable oil and olive oil. Other polyols including glycerol, pentaerithritol, and various saccharides were used for transesterification. The resulting fatty polyols were used as monomers in the polyester condensations described in Example 1.

Example 11

Extension of Polymer Chains with Hexamethylene Diisocyanate (HMDI)

Prepolymers composed of adipic acid, butanediol and ricinoleic acid and/or castor oil were extended with hexamethylene diisocyanate (HMDI).

A prepolymer of adipic acid, butanediol and 5% w/w castor oil having a molecular weight of 9,500 was mixed with 10% w/w hexamethylene diisocyanate (HMDI) and melt polymerized for 15 minutes at 155° C. This process resulted in the incorporation of greater than 90% of the HMDI into the polymer. HMDI reacts with the free hydroxyl groups in the prepolymer leaving an unreacted isocyanate group available for further reaction, i.e. crosslinking. Injection molding of the HMDI treated prepolymer at 160° C. resulted in a strong, non-breakable translucent tube. The tube was cured at 180° C. for 10 minutes.

Alternatively, the prepolymer composed of adipic acid, butanediol and 5% w/w castor oil was mixed with 10% w/w HMDI and injection molded at 200° C. to form the desired tube. The tube was cured at 200° C. for 30 minutes.

Additive such as fillers, stabilizers, colorants, fragrances and radical scavengers can be added to the prepolymer mixture prior to injection molding.

The mechanical characteristics for a variety of polymers formed by polymerizing prepolymers of adipic acid, butanediol and varying percentages of ricinoleic acid or castor oil and HMDI are listed in Table 4.

TABLE 4

Mechanical Characteristics for Polymers formed from Polymerization of prepolymers of adipic acid, butanediol, ricinoleic acid or castor oil, and HMDI

| Prepolymer | Solubility in CHCl$_3$ | Mechanical characteristics |
|---|---|---|
| A. Reaction of Prepolymers with 5% w/w HMDI at 155° C. for 0.5 h ||| 
| Adipic acid-Butanediol-ricinoleic acid 5% w/w | crosslinked | Tough pliable, film forming |
| Adipic acid-Butanediol-ricinoleic acid 10% w/w | crosslinked | Tough pliable, film forming |
| Adipic acid-Butanediol-ricinoleic acid 15% w/w | Soluble | Tough pliable, film forming |
| Adipic acid-Butanediol-castor oil 5% w/w | crosslinked | Tough pliable, film forming |
| Adipic acid-Butanediol-castor oil 10% w/w | crosslinked | Brittle pliable, film forming |
| B. Reaction of Prepolymers with 10% w/w HMDI at 155° C. for 0.5 h |||
| Adipic acid-Butanediol | crosslinked | Tough, Flexible |
| Adipic acid-Butanediol-ricinoleic acid 5% w/w | crosslinked | Tough, Flexible |
| Adipic acid-Butanediol-ricinoleic acid 10% w/w | Soluble | Brittle |
| Adipic acid-Butanediol-castor oil 15% w/w | Soluble | Brittle |
| Adipic acid-Butanediol-castor oil 5% w/w | crosslinked | Tough, Flexible |

Example 11

Curing Polyol Acrylate Prepolymer

Prepolymers having free hydroxyl or amine groups are reacted with acrylic anhydride or with methacrylic acid to form a prepolymer having acrylic or methacrylic side groups available for further polymerization. The prepolymer having between about 0.1% and 5% acrylate groups is mixed with up to 5% w/w ethylene glycol dimethacrylate, divinyl benzene or ethylene diacrylamide and about 1% benzoyl peroxide w/w. The mixture was melt molded into tubes and cured at 70° C. for 5 hours to induce crosslinking of the polymer chains.

We claim:

1. A biodegradable medical device comprising a hydrolytically degradable polymer in a form selected from the group consisting of containers, tubular devices, filaments, and sheets and structural components thereof,
    wherein the polymer comprises aliphatic carboxylic acid monomers, aliphatic dial monomers, and fatty acid monomers, and
    wherein the mole ratio of carboxylic acid monomer, aliphatic diol monomer, and fatty acid monomer is selected so the medical device does not degrade for 20 days at 37° C. in a buffer solution of pH 7.4, but does begin to degrade when placed in moist agricultural soil at 37° C. for one month.

2. The medical device of claim 1 selected from the group consisting of test tubes, syringes, tubing, catheters, shunts, collection bags and packaging materials.

3. The medical device of claim 1, wherein the polymer is biocompatible.

4. The medical device of claim 3, wherein the device does not absorb fluids or solids that are stored in the device.

5. The device of claim 1, wherein the polymer does not contain metals selected from the group consisting of antimony, tin, and titanium.

6. The device of claim 1, wherein the hydrolytically degradable polymer is selected from the group consisting of poly(butylenes adipate ricinoleate), poly(butylenes succinate ricinoleate), poly(butylenes adipate castor oil), poly(butylenes succinate castor oil), poly(butylenes adipate oleate), poly(butylenes succinate oleate), poly(butylenes adipate erucicuate), poly(butylenes adipate erucicuate), poly(butylenes adipate linolenate), poly(butylenes succinate linolenate), poly(hexane adipate ricinoleate), poly(hexanes succinate ricinoleate), poly(hexane adipate castor oil), poly (hexane succinate castor oil), poly (hexane adipate oleate), poly(hexane adipate erucicuate), poly(hexane succinate erucicuate), poly(hexane adipate linolenate), and poly(hexane succinate linolenate).

7. The device of claim 1, wherein the sheet is a medical fabric selected from the group consisting of gauzes, fabrics, gowns, surgical drapes, and surgical sponges.

8. The device of claim 1, wherein the hydrolytically degradable polymer further comprises a branching agent in an effective amount to increase the number of reactive functional groups available for crosslinking.

9. The device of claim 8, wherein the branching agent is a polyol.

10. The device of claim 9, wherein the polyol is selected from the group consisting of 1,1,1-trimethylolpropane, triethanolamine, glycerol, sorbitan, pentaerythritol, polyvinyl alcohol; mono, di, and polysaccharides, and triglycerides which have been partially esterified with a polyol.

11. The device of claim 1, wherein the hydrolytically degradable polymer further comprises a chain extension agent in an effective amount to increase the mechanical strength and processability of the polymer compared to the same polymer formed in the absence of the chain extension agent.

12. The device of claim 11, wherein the chain extension agent is a molecule having two or more reactive functional groups selected from the group consisting of isocyanates, epoxides, anhydrides, acid chlorides, esters, and aldehydes.

13. The device of claim 12, wherein the chain extension agent is a diisocyanate.

14. The device of claim 13, wherein the diisocyanate is selected from the group consisting of, 6-hexamethylene diisocyanate, 1,4-tertramethylene diisocyanate, ethylene diisocyanate and 1,12-dodecane diisocyanate, 5-isocyanato-1-(isocyanatomethyl)-1,3,3-trimethylcyclohexane, 1,3-bis (1-isocyanato-1-methylethyl)benzene, cyclohexane-1,3-diisocyanate, cyclohexane-1,4-diisocyanate, 4,4'-diisocyanatodicyclohexylmethane, 2,4-diisocyanatodicyclohexylmethane, 1,3phenylene diisocyanate, 1,4-phenylene diisocyanate and mixtures thereof.

15. The device of claim 11, wherein the chain extension agent is a vinyl group.

16. The device of claim 15, wherein the vinyl group is selected from the group consisting of acrylate and methacrylate.

17. The device of claim 1, wherein the hydrolytically degradable polymer is a polyester comprising a carboxylic acid having two or more carboxylic acid groups, an aliphatic alcohol having two or more hydroxy groups, a fatty acid, and a polyfunctional branching agent to increase the number of reactive functional groups available for cross linking.

18. The device of claim 17, wherein the polyfunctional branching agent is a polyol selected from the group consisting of 1,1,1-trimethylolpropane, triethanolamine, glycerol, sorbitan, pentaerythritol, polyvinyl alcohol; mono, di, and polysaccharides, and triglycerides which have been partially esterified with a polyol.

19. The device of claim 18, wherein the fatty acid monomer is present in an effective amount to increase the elasticity of the polyester.

20. The device of claim 19, wherein the fatty acid monomer is selected from the group consisting of ricinoleic acid, dimeric oleic acid, and dimeric erucic acid.

21. The device of claim 1, wherein the hydrolytically degradable polymer further comprises an additive in an effective amount to increase the mechanical strength of the polymer.

22. The device of claim 1, further comprising a non-biodegradable biocompatible polymer.

23. The device of claim 22, wherein the device comprises a core or structural elements formed of the non-biodegradable polymer within a matrix of the hydrolytically degradable polymer.

24. The device of claim 22, wherein the device comprises a core or structural elements formed of the hydrolytically degradable polymer within a matrix of the non-biodegradable polymer.

25. The device of claim 22, further comprising a polymer coating.

26. The device of claim 25, wherein the device comprises a core or structural elements formed of the hydrolytically degradable polymer, and wherein the polymer coating comprises the non-biodegradable polymer and coats the surface of the core or structural elements.

27. The device of claim 25, wherein the device comprises a core or structural elements formed of the non-degradable polymer, and wherein the polymer coating comprises the hydrolytically degradable polymer and coats the surface of the core or structural elements.

28. The device of claim 25, wherein the polymer coating has a thickness from about 0.1 microns to about 200 microns.

29. The device of claim 25, wherein the polymer coating is selected from the group consisting of biodegradable and slowly biodegradable polymer coatings.

30. A method of making a biodegradable disposable medical device, comprising providing a hydrolytically degradable polymer comprising aliphatic carboxylic acid monomers, aliphatic diol monomers, and fatty acid monomers, wherein the mole ratio of carboxylic acid monomer, aliphatic dial monomer, and fatty acid monomer is selected so the medical device does not degrade for 20 days at 37° C. in a buffer solution of pH 7.4, but does begin to degrade when placed in moist agricultural soil at 37° C. for one month, and process forming the hydrolytically degradable polymer into the medical device or component thereof.

31. The method of claim 30, wherein the process forming is selected from the group consisting of injection molding, extrusion coating, solvent casting, melt casting and melt spinning.

32. The method of claim 30, further comprising process coating the medical device with a polymer coating, wherein the polymer coating is biodegradable, slowly biodegradable, or non-biodegradable.

33. The method of claim 32, wherein the process coating occurs at a time selected from the group consisting of before process forming of the medical device, during process forming of the medical device, and after process forming of the medical device.

34. The method of claim 32, wherein the process coating is selected from the group consisting of melt extrusion, melt casting, and solvent casting.

35. The method of claim 33, wherein the hydrolytically degradable polymer is process coated before process forming of the medical device, the method comprising processing the hydrolytically degradable polymer into a sheet, process coating one or both sides of the sheet with a polymer coating and forming the polymer into a medical device.

36. A biodegradable polymerizable prepolymer comprising a dicarboxylic acid monomer, a diol monomer, and a bifunctional fatty acid monomer, wherein the molecular weight of the prepolymer is greater than 5,000 Da.

37. The prepolymer of claim 36, wherein the dicarboxylic acid is selected from the group consisting of adipic acid, sebacic acid, malonic acid, succinic acid, glutaric acid, pimelic acid, suberic acid, azelaic acid, fumaric acid, itaconic acid, maleic acid and combinations thereof.

38. The prepolymer of claim 36, wherein the diol is selected from the group consisting of 1,2-ethanediol, 1,3-propanediol, 1,4-butanediol, 1,5-pentenediol, 1,5-pentanediol, neopentyl glycol, 1,6-hexanediol, 1,7-heptanediol, 1,8-octanediol, 1,10-decanediol, 2-methyl-1,3-propanediol, 2,2-dimethyl-1,3-propanediol, 3-methyl-1,5-pentanediol, 2-butyl-2-ethyl-1,3-propanediol, 2-butene-1,4-diol and 2-butine-1,4-diol, and ether diols.

39. The prepolymer of claim 36, wherein the fatty acid monomer is selected from the group consisting of ricinoleic acid, dimeric oleic acid, dimeric erucic acid and combinations thereof.

40. The prepolymer of claim 36, further comprising a branching agent in an effective amount to increase the number of free hydroxy groups available on the prepolymer for crosslinking.

41. The prepolymer of claim 40, wherein the branching agent is selected from the group consisting of 1,1,1-trimethylolpropane, triethanolamine, glycerol, sorbitan, pentaerythritol, mannitol, sucrose, sorbitol, and polyvinylalcohol.

42. The prepolymer of claim 36, further comprising a chain extension agent.

43. The prepolymer of claim 42, wherein the chain extension agent is a molecule having two or more reactive functional groups selected from the group consisting of isocyanates, epoxides, anhydrides, acid chlorides, esters, and aldehydes.

44. A method of making a polymerizable biodegradable prepolymer comprising a dicarboxylic acid monomer, a diol monomer, and a bifunctional fatty acid monomer, comprising reacting the dicarboxylic acid monomer, the dial monomer, and the bifunctional fatty acid monomer in the presence of a mineral acid to form the prepolymer.

45. The method of claim 44, further comprising reacting the prepolymer with a branching agent.

46. The method of claim 44, further comprising reacting the prepolymer with a chain extension agent.

47. The method of claim 44, wherein the mineral acid is sulfuric acid or phosphoric acid.

48. The device of claim 5, wherein the polymer is synthesized utilizing a mineral acid.

49. The prepolymer of claim 38, wherein the ether diol is selected from the group consisting of diethylene glycol, triethylene glycol, tetraethylene glycol, dibutylene glycol, tributylene glycol, tetrabutylene glycol, dihexylene glycol, trihexylene glycol, tetrahexylene glycol, and oligomer mixtures of alkylene glycols.

* * * * *